Figure 4:
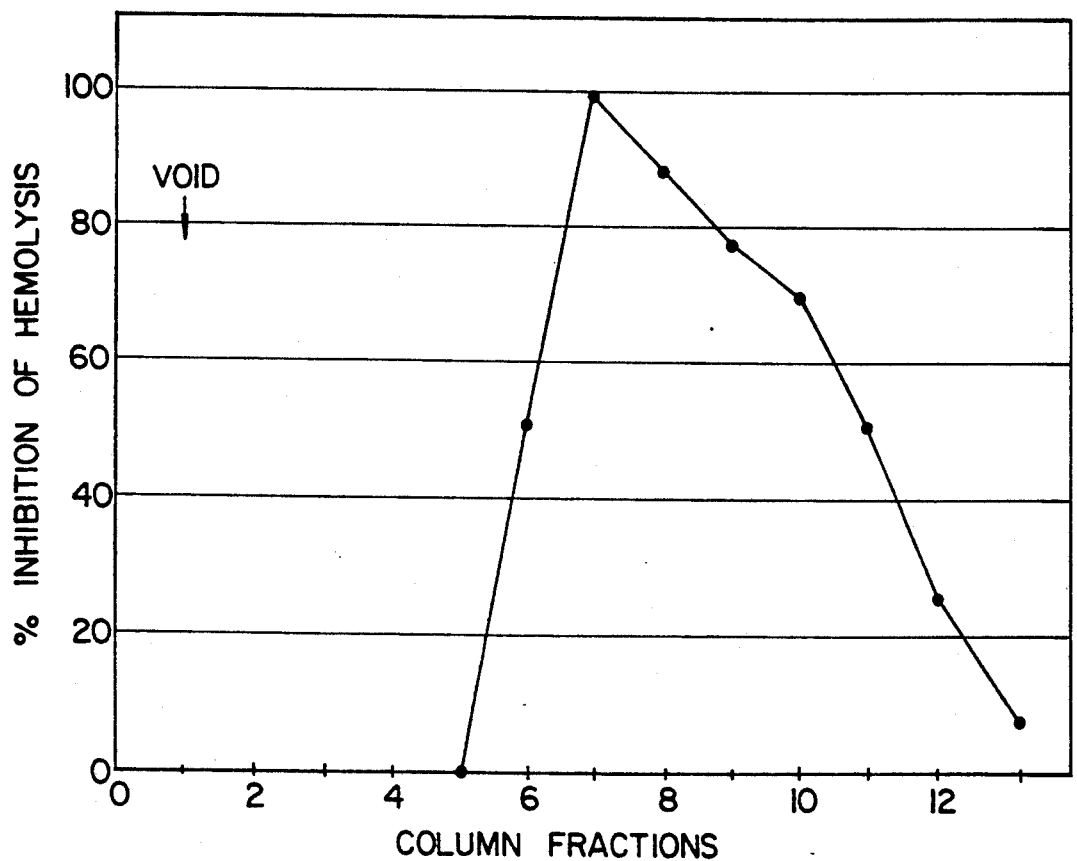
Figure 5:
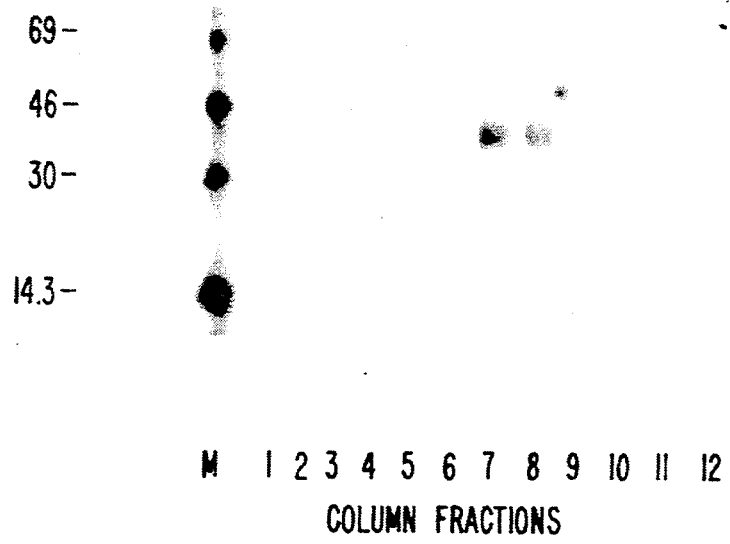

United States Patent [19]

Kotwal et al.

[11] Patent Number: 5,157,110
[45] Date of Patent: Oct. 20, 1992

[54] SYNTHETIC, ANTI-COMPLEMENT PROTEIN

[75] Inventors: Girish Kotwal; Bernard Moss, both of Bethesda, Md.

[73] Assignee: The Government of the United States of America, Washington, D.C.

[21] Appl. No.: 239,208

[22] Filed: Aug. 20, 1988

[51] Int. Cl.⁵ ............................................. C07K 13/00
[52] U.S. Cl. ................................... 530/350; 530/826; 930/220
[58] Field of Search .................. 530/350, 826; 514/12

[56] References Cited

PUBLICATIONS

Mallon & Holowczak "Vaccinia Virus Antigens on the Plasma Membrane of Infected Cells" Virology 141 201–220 (Mar. 1985).

Primary Examiner—Garnette D. Draper
Assistant Examiner—Nina Ossanna
Attorney, Agent, or Firm—Townsend and Townsend

[57] ABSTRACT

A substantially pure, synthetic protein possessing anti-complement property and a DNA sequence encoding said protein are described.

5 Claims, 5 Drawing Sheets

M 1 2 3
69K→
46K→
30K→
14K→
FIG. IA.
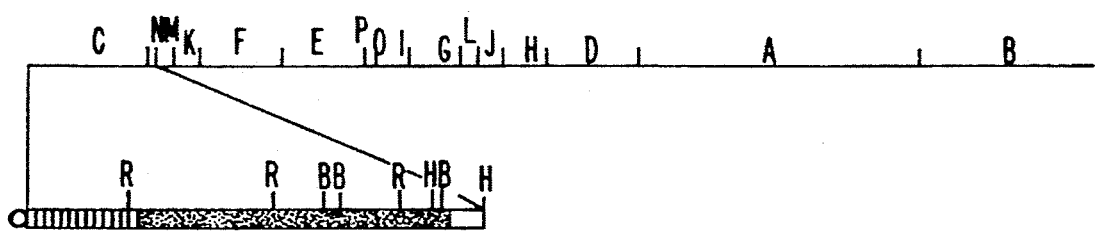
FIG. IB.

FIG. 2A.

```
TTTTATTTGTACGATGTCCAGGATATAAACATTTTTACGGATATAACATAAATATGAAGGTGGAGAGCGTGACGTTCCTGACATTGTTGGGAATAGGATGCGTTCTATCATGCTGTACTATT
         10        20        30        40        50        60        70        80        90       100       110       120
                                                              M   K   V   E   S   V   T   F   L   T   L   L   G   I   G   C   V   L   S   C   T   I
                                                                                                                               I>

P   S   R   P   I   N   M   K   F   K   N   S   Y   E   T   D   A   N   A   N   Y   N   I   G   D   T   I   E   Y   L   C   L   P   G   Y   R   K   Q   K   M
CCGTCACGACCATTAATATGAAATTTAAGAATTTAAGAATTTAGAAACAGATGCAAATGCTAATTACAATAGGAGACACTATAGAATATCTATGTCTACCTGGATACAGAAGCAAAAAATG
        130       140       150       160       170       180       190       200       210       220       230       240

G   P   I   Y   A   K   C   T   G   T   G   W   T   L   F   N   Q   C   I   K   R   R   C   P   S   P   R   D   I   D   N   G   Q   L   D   I   G   G   V   D
GGACCTATATATGCTAAATGTACAGGTACTGGATGGACTCTTTAATCAATGTATTAAACGGAGATGCCCATCGCCTCGAGATATGATATGGCCAACTTGATATTGGTGGAGTAGAC
        250       260       270       280       290       300       310       320       330       340       350       360

F   G   S   S   I   T   Y   S   C   N   S   G   Y   H   L   I   G   E   S   K   S   Y   C   E   L   G   S   T   G   S   M   V   W   N   P   E   A   P   I   C
TTTGGCTCTAGTATAACGTACTCTTGTAATAGTGGCTATCATCTTGTAATCTAAATCGTATTGTGAATTAGGATCTACTGGATCTATGGTATGGAATCCCGAGGCACCTATTTGT
        370       380       390       400       410       420       430       440       450       460       470       480
III>
 E   S   V   K   C   Q   S   P   P   S   I   S   N   G   R   H   N   G   Y   E   D   F   Y   T   D   G   S   V   V   T   Y   C   N   S   G   Y   S   L   I
GAATCTGTTAAATGCCAATCCCCTCCAATCTCAAATGGAAGACATAATCCAAGGAAGACATGATAACGACGGAAGACGTTGTAACTTATAGTTGCAATAGTGGATATTCGTTGATT
        490       500       510       520       530       540       550       560       570       580       590       600
                                                                         IV>
 G   N   S   G   V   L   C   S   G   E   W   S   D   P   P   T   C   Q   I   V   K   C   P   H   P   T   I   S   N   G   Y   L   S   S   G   F   K   R   S
GGTAACTCTGGTGTCCTGTGTTCAGGAGGAGAATGGTCCGATCCACCACGTGTCAGATTGTTAAATGTCCACATCCTACAATATCAAACGGATACTTGTCTAGCGGGTTAAAAGATCA
        610       620       630       640       650       660       670       680       690       700       710       720

Y   S   Y   N   D   N   V   D   F   K   C   K   Y   G   Y   K   L   S   G   S   S   S   T   C   S   P   G   N   T   W   K   P   E   L   P   K   C   V   R
TACTCATACAACGACAACGTAGACTTTAAGTGCAAGTACGGATATAAACTATCTGGTCTCCAGGAAATACATGGAAGCCGAACTTCAAATGTGTACGC
        730       740       750       760       770       780       790       800       810       820       830       840
```

FIG. 2B.

GENERAL CONSENSUS SEQUENCE OF 60 AMINO ACID REPEAT SUPERFAMILY:

```
---C--P--------Y/F-C---G--------G-W----C---A/P-C-
   1                                             60
```

```
         10        20        30        40        50        60        70        80        90
MKVESVTFLTLLGIGCVLSCCTIPSRPINMKFNSVETD-ANANYNIGDTIEYLCLPGYRKQKMGPIYAKCTGTG-WTLFNQCIKRRCPSPR
  ::  : ::   ::::   ::::::::::  ::: :   :::::: ::  : :::::  : ::
               NCG-PP-P-TLSFAAPMDITLTETRFKTGTTLKYTCLPGYVRSHSTQTLT-CNSDGEWVYNTFCIYKRCRHPG
               1*                                       *                 *    *

100       110       120       130       140       150       160       170       180
DIDNGQLDI-GGVDFGSSITYSCNSGYHLIGESKSYCELGSTGSMVWNPEAPICESVKCQSPPSISNGRHNGYEDFYTDGSVVTYSCNSGY
 : ::::::  :::::::                  :::  ::::: :::::::::::::::::::
ELRNGQVEIKTDLSFGSQIEFSCSEGFFLIGSTTSRCEVQDRG-VGWSHPLPQCEIVCKPPPDIRNGRHSGEENFYAYGFSVTYSCDPRF
                *                          *              *               *

190       200       210       220       230       240       250       260
SLIGNSGVLCSG------GEW-SDPPTCQIVKCPHPTISNGYLSSGFKRSYSYNDNVDFKCKYGYKLSGSSSTCSPGNTWKPELPKCVR
::  :::   :::::::  ::  ::::::: :: :::::  :::
SLLGHASISCTVENETIGVWRPSPPTCEKITCRKPDVSHGEMVSGFGPIYNYKDTIVFKCQKGFVLRGSSVIHCDADSKWNPSPPACEP * 248
  *                        *                  *                *
```

FIG. 3.

SYNTHETIC, ANTI-COMPLEMENT PROTEIN

The present invention is related generally to the identification and characterization of new proteins. More particularly, the present invention is related to the identification of a gene and the encoded protein which possesses anti-complement properties. There are no known synthetic or microbial proteins capable of specifically inhibiting the complement cascade.

SUMMARY OF THE INVENTION

It is, therefore, an object of the present invention to provide substantially pure, isolated protein specifically inhibiting the complement cascade.

It is a further object of the present invention to provide a nucleotide sequence directing the synthesis of the novel protein of the present invention when cloned in a suitable expression vector.

It is another object of the present invention to provide a therapeutic composition and method for treating or controlling conditions resulting from the action of complement, by providing a synthetic inhibitor of complement.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1*a* shows the results of analysis of the medium from RK-13 cells infected either with standard vaccinia virus strain WR or with deletion mutant 6/2 at an moi of 50 pfu/cell in the presence of [$^{35}$S]-methionine containing minimal medium (RPMI) for 16 h, by 12.5% SDS-PAGE. Lane M has [$^{14}$C]-labeled molecular weight markers. Lanes 1 to 3 show the results of labeled medium from uninfected RK-13 cells, standard vaccinia virus infected cells and mutant 6/2 infected cells, respectively. The arrow heads indicate the two protein bands corresponding to the 35 KDa and 12 KDa proteins that are present only in the medium from the standard virus infected cells.

FIG. 1*b* shows the Hind III map of the vaccinia virus WR strain with the enlarged left end indicating the coding information absent from the genome of mutant 6/2 (the shaded area). The vertical bars indicate the inverted terminal repeats which are intact in mutant 6/2. The arrow indicates the direction and the position of the 35K protein. The fine mapping was made possible by the $NH_2$-terminal analysis of the protein and matching the sequence to that of the predicted sequence of the open reading frame as shown in FIG. 2*a*. The letters R, B, and H indicate the restriction sites Eco R1, Bam HI and Hind III, respectively.

FIG. 2*a* shows the nucleotide sequence of the vaccinia virus (WR strain) 35K gene in 5'-3' direction. The predicted coding sequence starting at position 52 (starting codon, ATG) to position 840 (the last codon preceding the stop codon) has been translated into the corresponding amino acid sequence which is shown above the nucleotide sequence in the one letter code. The nucleotide sequence was determined on both strands by generating overlapping fragments using exonuclease III digestion and cloning them into m13 vectors and sequencing of the single strands by dideoxy-chain termination technique. The analysis was done using the Beckman microgenie program. The potential late transcription start site TAAATATG starting at nucleotide 47 has 2 extra nucleotides in comparison to the typical late transcription start site TAAATG and the potential early transcription termination signal TTTTTNT starts at nucleotide 543. $NH_2$-terminal sequence analysis of the purified 35K secretory protein by the Applied Biosystem gas-phase 477A protein sequencing system using the program version 1.5 was carried out on 35K band transferred to an Immobilon filter from a 12.5% SDS-PAGE gel. The sequence of the first 18 amino acids derived from this procedure aligned to the predicted sequence beginning with the cysteine in position 20. The underlined amino acids represent the amino acid assignments that were possible from the protein sequence. The downward arrow indicates the site at which the signal peptide is cleaved. The numeral I, II, III and IV indicate the start of the 60 amino acid tandem repeating units found in the protein which have the consensus sequence shown in FIG. 2*b*.

FIG. 3 shows the alignment of the deduced amino acid sequence of the vaccinia 35K secretory protein and the human C4b-binding protein. Identical amino acids are indicated by colons and conservative changes by periods. The similarity was found using the FASTP program of Lipman and Pearson searching the amino acid bank library.

FIG. 4 shows the elution of the 35K inhibitor of complement mediated hemolysis from a G-100 Sephadex column. The void volume of the column is indicated. Individual fractions from the column were tested for inhibition of complement mediated hemolysis.

FIG. 5 shows the elution of proteins from the same G-100 Shephadex column used to measure inhibition of complement mediated hemolysis in FIG. 4. The proteins made by vaccinia virus infected RK-13 cells were metabolically labeled with [$^{35}$S]methionine and an autoradiograph is shown. The mass of marker proteins in kilodaltons is shown on the left.

DETAILED DESCRIPTION OF THE INVENTION

The above and various other objects and advantages of the present invention are achieved by the nucleotide sequence starting with nucleotide 52 and the corresponding amino acid sequence as shown hereunder:

```
TTTTTATTATTTGTACGATGTCCAGGATAACATTTTTACGGATAAATAAATATGAAGGTGGAGAGCGT
          10        20        30        40        50        60

GACGTTCCTGACATTGTTGGGAATAGGATGCGTTCTATCATGCTGTACTATT
                    70        80        90        100       110       120

CCGTCACGACCCATTAATATGAAATTTAAGAATAGTGTGGAGACTGATGCTAATGCTAATTACAACA
          130       140       150       160       170       180.
```

-continued

```
          TAGGAGACACTATAGAATATCTATGTCTACCTGGATACAGAAAGCAAAAAATG
          190       200       210       220       230       240

GGACCTATATATGCTAAATGTACAGGTACTGGATGGACACTCTTTAATCAATGTATTAAACGGAGAT
250       260       270       280       290       300

GCCCATCGCCTCGAGATATCGATAATGGCCAACTTGATATTGGTGGAGTAGAC
                    310       320       330       340       350       360

TTTGGCTCTAGTATAACGTACTCTTGTAATAGCGGATATCATTTGATCGGTGAATCTAAATCGTATT
370       380       390       400       410       420

GTGAATTAGGATCTACTGGATCTATGGTATGGAATCCCGAGGCACCTATTTGT
              430       440       450       460       470       480

GAATCTGTTAAATGCCAATCCCCTCCATCTATATCCAACGGAAGACATAACGGATACGAGGATTTTT
490       500       510       520       530       540

ATACCGATGGGAGCGTTGTAACTTATAGTTGCAATAGTGGATATTCGTTGATT
                550       560       570       580       590       600

GGTAACTCTGGTGTCCTGTGTTCAGGAGGAGAATGGTCCGATCCACCCACGTGTCAGATTGTTAAAT
610       620       630       640       650       660

GTCCACATCCTACAATATCAAACGGATACTTGTCTAGCGGGTTTAAAAGATCA
                670       680       690       700       710       720

TACTCATACAACGACAATGTAGACTTTAAGTGCAAGTACGGATATAAACTATCTGGTTCCTCATCAT
730       740       750       760       770       780

CTACTTGCTCTCCAGGAAATACATGGAAGCCGGAACTTCCAAAATGTGTACGC
              790       800       810       820       830       840
```

Amino acid sequence:

1 
MK V E S V T F L TL L G I G C V L SC C T I
SIGNAL SEQUENCE ABSENT IN THE 35K PROTEIN FOUND IN THE MEDIUM

P S R P I N M K F K N S V E T D A N A N Y N I G D T I E Y L C L P G Y R K Q K M

G P I Y A K C T G T G W T L F N Q C I K R R C P S P R D I D N G Q L D I G G V D

F G S S I T Y S C N S G Y H L I G E S K S Y C E L G S T G S M V W N P E A P I C

E S V K C Q S P P S I S N G R H N G Y E D F Y T D G S V V T Y S C N S G Y S L I

G N S G V L C S G G E W S D P P T C Q I V K C P H P T I S N G Y L S S G F K R S

Y S Y N D N V D F K C K Y G Y K L S G S S S S T C S P G N T W K P E L P K C V R

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "substantially" pure as used herein means that the synthetic protein is as pure as can be obtained by employing standard, conventional purification techniques known to one of ordinary skill in the art. The term "complement" as used herein means the complement cascade as is well known and understood by one of ordinary skill in the art and the term "anti-complement", therefore, means interfering with normal complement function.

The term "synthetic" protein as used herein means that given the amino acid sequence, the protein is synthesized by any suitable means known to one of ordinary skill in the art such as by recombinant genetic technology, chemical synthesis (e.g., by commercial polypeptide synthesizers) and the like, the method of synthesis per se not being a part of the present invention. Only as an illustration, and not as a limitation, a method of synthesizing the protein of the present invention by infection of tissue culture cells by vaccinia virus is now exemplified.

RK-13 cells (ATCC CCL 37) are grown to confluency in 150 cm² tissue culture flasks with Eagle minimal essential medium (MEM) containing 10% fetal bovine serum at 37° C. The cells are infected with vaccinia virus strain WR (ATCC VR-119) in 3 ml of MEM containing 2.5% fetal bovine serum for 2 hours. The cells monolayers are then washed extensively with serum-free medium in order to remove the inoculum and residual serum proteins. The washed cells are then overlayed with 10 ml of serum-free MEM per flask and then incubated at 37° C. for a further 20 hours. The medium is then harvested, clarified by low speed centrifugation (2,500 rev/min in an H6000A rotor in a Sorvall RC-3B centrifuge) for 10 min at 4° C. The pooled medium is then concentrated ten-fold and partially purified with an Amicon filter with a 10,000 molecular weight cut-off. The concentrate is dialyzed at 4° C. against buffer 30 mM NaCl, 10 mM EDTA, 10 mM Tris-HCl pH 8.6 using a membrane with an 8,000 molecular weight cut-off.

Further purification can be achieved by a variety of column chromatography procedures. The dialyzed material is applied to a column of DEAE Biogel that has been equilibrated with 25 mM NaCl, 5 mM EDTA, 20 mM Tris-HCl, pH 8.6 and then eluted with a gradient of 0.03 to 0.3M NaCl. Fractions are monitored by SDS polyacrylamide gel electrophoresis and those containing the 35K protein are pooled. The pooled fractions may then be applied to a Biorex 70 column that is equilibrated with 0.02M sodium phosphate buffer pH 7.2 and eluted with a gradient from 0 to 0.7M sodium chloride in 0.02M sodium phosphate. Fractions are monitored as above. Peak fractions are further purified by gel filtration using a Sephadex G-100 column equilibrated with 141 mM NaCl, 0.15 mM CaCl$_2$, 0.5 mM MgCl$_2$, 1.8 mM sodiumbarbital, 3.1 mM barbituric acid, pH 7.3–7.4.

Having obtained a substantially pure product, the specific anti-complement activity of the product is measured using standard procedures and commercially available material as follows. Sensitized sheep red blood cells (Diamedix Corporation, catalog no. 789-001) in 150 ul volumes is dispensed into the wells of a 96 microwell plate (Nunc catalog no.